United States Patent [19]

Waldhoff et al.

[11] Patent Number: 4,904,389

[45] Date of Patent: Feb. 27, 1990

[54] PROCESS FOR THE SEPARATION OF DICARBOXYLIC ACIDS

[75] Inventors: Heinrich Waldhoff, Langenfeld; Joachim Schindler, Hilden; Holger Viehweg, Langenfeld, all of Fed. Rep. of Germany

[73] Assignee: Henkel Kommanditgesellschaft auf Aktien, Duesseldorf, Fed. Rep. of Germany

[21] Appl. No.: 208,342

[22] Filed: Jun. 17, 1988

[30] Foreign Application Priority Data

Jun. 19, 1987 [DE] Fed. Rep. of Germany ....... 3720261

[51] Int. Cl.⁴ .................. C07C 51/42; C07C 57/13; C07C 55/02; B01D 13/00

[52] U.S. Cl. ................... 210/637; 210/639; 210/651; 210/741; 210/743; 435/142

[58] Field of Search .............. 435/142; 210/637, 639, 210/651, 743, 741

[56] References Cited

U.S. PATENT DOCUMENTS

| | | | |
|---|---|---|---|
| 3,823,070 | 7/1974 | Minato et al. | 195/28 R |
| 3,843,466 | 10/1974 | Akabori et al. | 435/142 |
| 4,075,093 | 2/1978 | Walch et al. | 210/639 |
| 4,220,720 | 9/1980 | Taoka et al. | 435/142 |
| 4,339,536 | 7/1982 | Kato | 435/142 |
| 4,584,057 | 4/1986 | Rowe et al. | 210/639 |
| 4,608,338 | 8/1986 | Hsieh | 435/142 |
| 4,624,920 | 11/1986 | Inoue et al. | 435/142 |
| 4,663,048 | 5/1987 | Tanaka et al. | 435/639 |

FOREIGN PATENT DOCUMENTS

| | | | |
|---|---|---|---|
| 2951177 | 7/1984 | Fed. Rep. of Germany . | |
| 0162991 | 12/1980 | Japan | 435/142 |
| 0011797 | 2/1981 | Japan | 435/142 |
| 0011798 | 2/1981 | Japan | 435/142 |
| 0015694 | 2/1981 | Japan | 435/142 |
| 0102191 | 6/1982 | Japan | 435/142 |
| 0105193 | 6/1982 | Japan | 435/142 |

OTHER PUBLICATIONS

Process Biochemistry, Mar./Apr. 1983, pp. 8–12.

*Primary Examiner*—Herbert J. Lilling
*Attorney, Agent, or Firm*—Ernest G. Szoke; Wayne C. Jaeschke

[57] ABSTRACT

A process for separation of multicomponent mixtures of dicarboxylic acids, especially, mixtures of $C_8$–$C_{24}$ saturated and unsaturated acids is derived from a fermentation process, in which an aqueous feed solution containing the mixture of dicarboxylic acids is adjusted in pH value depending on the permeability of the component to be separated and over 95% of the saturated component is separated from the unsaturated material by passing the mixture is content with a membrane filter.

22 Claims, No Drawings

PROCESS FOR THE SEPARATION OF DICARBOXYLIC ACIDS

BACKGROUND OF THE INVENTION

1. Field of the Invention

This invention relates to a process for the separation of dicarboxylic acids by membrane filtration.

2. Discussion of Related Art

Conventional processes for separating mixtures of dicarboxylic acids include crystallization, rectification and extraction. However, narrow limits are frequently imposed on the application of these processes on an industrial scale since the dicarboxylic acids to be separated differ only slightly in regard to the physical properties of relevance to these processes. In cases such as these, separation can often only be carried out incompletely and at considerable cost. This is always the case when relatively large carboxylic acid molecules only differ from one another in regard to a functional group or another comparable molecular parameter.

German Patent Publications Nos. 21 40 133 and 28 53 847 describe processes for the production of dicarboxylic acids by fermentation and for the purification thereof. The mixture of dicarboxylic acids which are formed are separated by chromatography in the form of their methyl esters solely for analytical characterization. A similar fermentative process is described in German Patent Publication No. 21 64 626. The mixtures of hydroxy, keto and dicarboxylic acids formed are separated by distillation of the alkyl esters under reduced pressure.

German Patent Publication No. 29 51 177 describes the purification of dicarboxylic acids produced by fermentation by recrystallization from a solvent. Fractional crystallization is another known method for the separation of dicarboxylic acid mixtures.

Membrane filtration is generally used for the separation of substances according to gram molecular weight.

On the other hand, it is known from Process Biochemistry, March/April 1983, pages 8–12, that the permeability of membranes to certain dissolved substances can be controlled through the choice of the pH value of the solution to be filtered. For example, the concentration of acetic acid or lactic acid in aqueous solution can be concentrated by means of a special membrane. However, there is no suggestion in this literature reference of a process for the specific separation of carboxylic acids and special dicarboxylic acids.

In the main, the above-mentioned processes for the separation of mixtures of dicarboxylic acids differing only slightly in their chemical structure are only suitable for laboratory quantities.

Accordingly, an object of the present invention is to provide a separation process for dicarboxylic acids which combines a high separation efficiency and increased capacity such that the process is suitable for use on a relatively large commercial scale.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, the present invention relates to a process for the separation of mixtures of dicarboxylic acids which comprises maintaining an aqueous solution of a mixture of dicarboxylic acids in a membrane filtration zone and adjusting the pH value of such solution such that the membrane filter is preferentially impermeable to at least one of the dicarboxylic acids. Preferably the membrane is made permeable by pH adjustment to less than 5% of at least one selected component of the mixture; and a filtrate is obtained containing the desired mixture of dicarboxylic acids from which at least 95% of the desired component acid has been eliminated.

This invention is based on the discovery that the permeability of membranes to dicarboxylic acids depends to a very large extent on the specific molecular properties of the acid as a function of the pH value of the solution to be filtered. For example, where a single double bond is present in the molecule of a dicarboxylic acid derived from a fatty acid, we have discovered that the permeability of the membrane to this molecule compared with the permeability of the corresponding saturated compounds is influenced by the pH value of the solution to such an extent that the process is useful for the separation of such mixtures on an industrial scale.

In one preferred embodiment, therefore, the process of this invention is used for the separation of mixtures of saturated and unsaturated dicarboxylic acids, preferably $\alpha,\omega$-dicarboxylic acids, more particularly containing 8 to 24 carbon atoms. The membrane is made impermeable to at least 95% of the quantity of saturated dicarboxylic acid through the choice of the pH value.

The components of the mixtures to be separated include saturated and olefinically mono- to tri-unsaturated, branched or unbranched dicarboxylic acids optionally containing further substituents. Examples of these compounds are octanedioic acid, nonanedioic acid, decanedioic acid, undecanedioic acid, dodecanedioic acid, tridecanedioic acid, tetradecanedioic acid, pentadecanedioic acid, hexadecanedioic acid, heptadecanedioic acid, octadecanedioic acid, nonadecanedioic acid, eicosanedioic acid, heneicosanedioic acid, docosanedioic acid, trieicosanedioic acid and tetraeicosanedioic acid and the analogous olefinically mono- to tri-unsaturated $\alpha,\omega$-dicarboxylic acids. In all of the cases mentioned, the olefinically unsaturated dicarboxylic acids may also be present in completely or partly epoxidized form.

The process is particularly suitable for the separation of mixtures formed by terminal oxidation of alkanes, primary alcohols, monocarboxylic acids or monocarboxylic acid esters by microorganisms, for example, as described in German Patent Application P 35 40 834. These reactions give mixtures which may correspond to the starting materials in their composition, i.e. in regard to chain length and in regard to the number and position of the double bonds.

For example, saturated, unbranched $\alpha,\omega$-dicarboxylic acids are separated from their mono- or di-unsaturated analogs.

If the mixtures of dicarboxylic acids are not present in aqueous solution, they are first brought into aqueous solution in order to carry out the process of this invention. Water-miscible organic solvents, for example ethanol, propanol, isopropanol, acetone, are useful for this purpose. The pH value of the solution are preferably adjusted with standard alkaline-reacting substances, for example alkali hydroxides or ammonia. The optimal pH value is chosen by determining the dependence of separation efficiency on the pH value of the solution to be filtered in preliminary tests. To this end, the expert will carry out the process of the invention at a number of pH values and will analytically characterize the filtrate to determine the efficiency of separation. For the separation of dicarboxylic acids, high separation efficiencies were observed in the preferred pH range from 4 to 11. Separation is carried out more preferably at a pH value in the range from pH 6.5 to pH 9.5, and highly favorable results are obtained at pH values in the range from 8 to 9.5.

Membranes of cellulose acetate, derivatives of cellulose acetate, such as cellulose acetobutyrate, and synthetic polymers, such as polimides and polyamides, are useful for the process of the invention. In one preferred embodiment of the process according to the invention, membranes of cellulose acetate are used. The pore diameters of the membranes used for the process of the invention are below 0.5 $\mu$m. Pore diameters below 0.25 $\mu$m are preferred. In this embodiment, the lower limit of the pore diameters of the membranes used in 0.1 $\mu$m. In addition to those membranes of the type normally used for microfiltration (pore diameters of the order of a few tenths of a $\mu$m), the process of this invention can also use membranes to the type used for ultrafiltration. In this case, pore diameters of the type used for the separation of substances having gram molecular weights above 500 dalton are useful.

The temperature at which membrane filtration is carried out is determined both by the viscosity of the solution and by the properties of the materials selected. The available temperature range is limited on the one hand by the freezing point of the solution to be filtered and on the other hand by the destabilization of the membrane at elevated temperatures.

In the interests of energy economy, the expert will preferably work at room temperature. On the other hand, the viscosity of the solution decreases with increasing temperature such that higher throughputs can be obtained at higher temperatures. The temperature range is generally between 0° C. and 120° C. and preferably between 20° C. and 60° C.

Another parameter of the process of the invention is the external pressure applied to the solution. By increasing the pressure, the throughput of the membrane filtration process is significantly increased. Thus, an external pressure of up to 20 bar is helpful when applied to the solution. In one particularly preferred embodiment of the process of the invention, an additional external pressure of up to 5 bar is applied.

Advantages of the process of this invention include the separation of individual components of dicarboxylic acid mixtures differing only slightly in regard to their molecular properties to an extent of at least 95% separation on an industrial scale at reasonable cost. It is thus possible to separate off unwanted secondary products for further processing of the dicarboxylic acids produced.

The advantages and effectiveness of the process according to the invention are demonstrated in the following Example.

EXAMPLE 10 ml of a fermenter solution containing approximately 10 g/l of $C_{16}$ $\alpha,\omega$-dicarboxylic acids (including approx. 2 g unsaturated species) were adjusted with sodium hydroxide to a pH value of 9. The solution was filtered through a Satorius Minisart NML membrane filter having a pore diameter of 0.2 $\mu$m. The filtrate was worked up by solid-liquid extraction using Sep-pak cartridges (Sep-pak) RP18, Millipore). The filtrate was analyzed by gas chromatography and by HPLC. The chromatogram of the filtered sample showed an elimination of greater than 95% of the saturated $C_{16}$ $\alpha,\omega$-dicarboxylic acid.

We claim:

1. A process for the separation of mixtures of dicarboxylic acids which comprises maintaining an aqueous feed solution of a multicomponent mixture of dicarboxylic acids in a membrane filtration zone, adjusting the pH value of said solution such that the membrane is made preferentially impermeable to at least one component of the dicarboxylic acid mixture, and recovering a dicarboxylic acid filtrate containing less of at least one component than said aqueous feed solution.

2. The process of claim 1 in which the pH value of said aqueous feed solution is adjusted to a value of from about 4 to about 11 in dependence upon the permeability of the component to be separated.

3. The process of claim 1 in which the pH value of said aqueous feed solution is adjusted to a value of from about 6.5 to about 9.5.

4. The process of claim 1 in which the pH value of said aqueous feed solution is adjusted to a value of from about 8 to about 9.5.

5. The process of claim 1 in which the membrane comprises a cellulose ester.

6. The process of claim 5 in which said cellulose ester comprises cellulose acetate or cellulose acetobutyrate.

7. The process of claim 1 in which the membrane comprises a polyamide or polyimide.

8. The process of claims 1 in which the pore diameter of said membrane is smaller than about 0.5 $\mu$m.

9. The process of claim 1 in which the pore diameter of said membrane is smaller than about 0.25 $\mu$m.

10. The process of claim 1 in which the pore diameter of said membrane is useful for the separation of substances having gram molecular weights above 500 dalton.

11. The process of claim 1 in which said aqueous feed solution contains a mixture of $\alpha,\omega$-dicarboxylic acids containing 8 to 24 carbon atoms.

12. The process of claims 1 in which said aqueous feed solution contains a mixture of saturated dicarboxylic acids and unsaturated dicarboxylic acids, and a filtrate is recovered which is depleted in saturated dicarboxylic acids.

13. The process of claim 1 in which said aqueous feed solution contains mixtures comprising unbranched, $\alpha,\omega$-dicarboxylic acids, or unsaturated, unbranched $\alpha,\omega$-dicarboxylic acids containing 1 to 3 double bonds.

14. The process of claim 1 in which alkali hydroxides or ammonia are used to adjust the pH value.

15. The process of claim 1 in which the membrane filtration zone is maintained at a temperature between the freezing point of the solution and the stability limit of the membrane.

16. The process of claim 1 in which the membrane filtration zone is maintained at a temperature between about 20° C. and about 60° C.

17. The process of claim 1 in which the membrane filtration zone is maintained at an external pressure up to about 5 bar.

18. The process of claim 1 in which the membrane filtration zone is maintained at an external pressure up to about 20 bar.

19. A process for the separation of mixtures of dicarboxylic acids which comprises maintaining an aqueous feed solution containing a mixture of saturated and unsaturated dicarobxylic acids in a membrane filtration zone, adjusting the pH value of said solution in dependence upon the permeability of the component to be separated, and recovering a filtrate depleted with respect to the saturated carboxylic acid.

20. The process of claim 19 in which the aqueous feed solution contains a mixture of saturate and unsaturated $\alpha,\omega$-dicarboxylic acids containing 8 to 24 carbon atoms, adjusting the pH value of the solution to between about 8 and about 9.5 and recovering a filtrate from which at least about 95% of the saturated acid has been eliminated.

21. The process of claim 19 in which said mixture of dicarboxylic acids comprises the reaction product of a fermentation process.

22. A process for the separation of mixtures of dicarboxylic acids which comprises (1) maintaining an aqueous feed solution of mixtures of saturated and unsaturated dicarboxylic acids produced by fermentation in a membrane filtration zone, wherein said membrane is comprised of cellulose esters; (2) adjusting the pH of said solution such that the membrane is made preferentially impermeable to at least one component of the dicarboxylic acid mixture; and (3) recovering a dicarboxylic acid filtrate containing less of at least one component than said aqueous feed solution.

* * * * *